(12) United States Patent
Oba (10) Patent No.: US 11,413,147 B2
(45) Date of Patent: Aug. 16, 2022

(54) VENTRICULAR REMODELING USING COIL DEVICES

(71) Applicant: Edwards Lifesciences Corporation, Irvine, CA (US)

(72) Inventor: Travis Zenyo Oba, Yorba Linda, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 136 days.

(21) Appl. No.: 16/549,133

(22) Filed: Aug. 23, 2019

(65) Prior Publication Data

US 2020/0107933 A1 Apr. 9, 2020

Related U.S. Application Data

(60) Provisional application No. 62/740,563, filed on Oct. 3, 2018.

(51) Int. Cl.
*A61F 2/24* (2006.01)
*A61B 17/04* (2006.01)

(52) U.S. Cl.
CPC ............ *A61F 2/2466* (2013.01); *A61F 2/246* (2013.01); *A61F 2/2454* (2013.01); *A61B 2017/0498* (2013.01); *A61F 2230/0091* (2013.01)

(58) Field of Classification Search
CPC ........ A61F 2/2478; A61F 2/2487; A61F 2/24; A61F 2/2442; A61F 2/2454; A61F 2/246; A61F 2/2469; A61F 2/2436; A61F 2/2439; A61F 2002/249; A61B 2017/0498
See application file for complete search history.

(56) References Cited

U.S. PATENT DOCUMENTS

| | | | |
|---|---|---|---|
| 8,043,368 B2 | 10/2011 | Crabtree | |
| 8,206,439 B2 | 6/2012 | Gomez Duran | |
| 8,382,653 B2 | 2/2013 | Dubi et al. | |
| 8,523,755 B2 | 9/2013 | Almog et al. | |
| 8,790,394 B2 | 7/2014 | Miller et al. | |
| 9,237,886 B2 | 1/2016 | Seguin et al. | |
| 9,364,326 B2 | 6/2016 | Yaron | |
| 9,656,009 B2 | 5/2017 | Kheradvar et al. | |
| 9,700,412 B2 | 7/2017 | Yaron et al. | |
| 10,034,749 B2 * | 7/2018 | Spence | A61F 2/2418 |
| 10,058,428 B1 * | 8/2018 | Neustadter | A61F 2/2487 |
| 2006/0167474 A1 | 7/2006 | Bloom et al. | |

(Continued)

OTHER PUBLICATIONS

Biswas, S. K., and Kalyani Vijayan. "Friction and wear of PTFE—a review." Wear 158.1-2 (1992): 193-211. (Year: 1992).*

(Continued)

*Primary Examiner* — Yashita Sharma
*Assistant Examiner* — Amanda M Barkan
(74) *Attorney, Agent, or Firm* — Jessica Anne Hudak (57) ABSTRACT

A method for treating a heart valve involves introducing a delivery catheter into a target ventricle of a heart, the delivery catheter having a coil device disposed at least partially therein, deploying a distal end of the coil device from the delivery catheter, navigating the distal end of the coil device behind a plurality of trabeculae carneae features associated with an inner wall of the ventricle to form one or more coils, and tightening the one or more coils to reduce a diameter of the target ventricle.

20 Claims, 5 Drawing Sheets

(56) References Cited

U.S. PATENT DOCUMENTS

2007/0255396 A1* 11/2007 Douk .................. A61F 2/2442
623/2.1
2010/0185278 A1  7/2010 Schankereli

OTHER PUBLICATIONS

Hvass et al., "The Papillary Muscle Sling for Ischemic Mitral Regurgitation." J Thorac Cardiovasc Surg. Feb. 2010;139(2):418-23.

* cited by examiner

VENTRICULAR REMODELING USING COIL DEVICES

RELATED APPLICATION

This application claims priority to U.S. Provisional Application No. 62/740,563, filed Oct. 3, 2018, and entitled VENTRICULAR REMODELING USING COIL DEVICES, the disclosure of which is hereby incorporated by reference in its entirety.

BACKGROUND

Field

The present disclosure generally relates to the field of ventricular remodeling.

Description of Related Art

Ventricular dilation can result in heart valve dysfunction, which may cause undesirable regurgitation and/or other health complications. Reduction in ventricular dilation can improve heart function in some patients.

SUMMARY

Described herein are one or more methods and/or devices to facilitate remodeling of the left ventricle and/or one or more other anatomical/cardiac chambers using one or more coil-type devices or structures.

In some implementations, the present disclosure relates to a method for treating a heart valve. The method comprises introducing a delivery catheter into a target ventricle of a heart, the delivery catheter having a coil device disposed at least partially therein, deploying a distal end of the coil device from the delivery catheter, navigating the distal end of the coil device behind a plurality of trabeculae carneae features associated with an inner wall of the ventricle to form one or more coils, and tightening the one or more coils to reduce a diameter of the target ventricle.

The coil device may comprise a cloth feature configured to promote ingrowth with tissue of the trabeculae carneae, and a wire associated with the cloth feature. In some embodiments, introducing the delivery catheter into the target ventricle is performed at least partially percutaneously. For example, the method may further comprise introducing the delivery catheter into an atrium of the heart through a transseptal puncture. The method may further comprise navigating the distal end of the coil device along a helical path around the inner wall of the ventricle to form the one or more coils. In some embodiments, the method further comprises navigating the distal end of the coil device around first and second papillary muscles associated with the ventricle, wherein said tightening the one or more coils approximates the first and second papillary muscles together.

In some embodiments, tightening the one or more coils comprises pulling the distal end of the coil device. For example, tightening the one or more coils further comprises pulling the distal end of the coil device back into the delivery catheter. The method may further comprise locking the coil device in a tightened state after tightening the one or more coils. For example, locking the coil device in the tightened state may be performed using a drawstring mechanism. The coil device may comprise material that promotes ingrowth with tissue of the inner wall of the ventricle. In some embodiments, the method further comprises anchoring the distal end of the coil device in tissue of the ventricle. For example, the tissue of the ventricle may be associated with an apex of the ventricle. In some embodiments, the coil device comprises material having a coefficient of friction of less than or equal to 0.1.

In some implementations, the present disclosure relates to a coil device comprising a wire having a distal end and a proximal end, and a cloth covering at least a portion of the wire, the cloth covering being configured to promote ingrowth thereof with biological tissue. The wire comprises memory metal that is pre-shaped to assume a helical coil shape in response to a stimulus, the helical coil shape having a diameter designed to provide a constricting force on a ventricle wall of a heart when the coil device is woven behind a plurality of tissue features of trabeculae carneae associated with the ventricle wall.

The stimulus may be a thermal stimulus corresponding to a thermal environment internal to the heart. In some embodiments, the coil device further comprises a locking mechanism configured to lock the coil device in a tightened state. For example, the locking mechanism may be configured to couple the distal end of the coil device to the proximal end of the coil device. The locking mechanism may comprise a drawstring mechanism including a cord lock component. For example, the cord lock component may be coupled to a first portion of the coil device and may be configured to receive and secure a second portion of the coil device thereto.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. Unless otherwise specifically noted, articles depicted in the drawings are not necessarily drawn to scale.

DETAILED DESCRIPTION

The headings provided herein are for convenience only and do not necessarily affect the scope or meaning of the claimed invention. The present disclosure relates to systems, devices, and methods for remodeling of the left ventricle and/or one or more other anatomical/cardiac chambers using one or more coil-type devices or structures.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

Embodiments of the present disclosure provide solutions relating to the treatment of certain structural heart conditions using coil-type device(s). Such coil devices can be used, for example, in remodeling dilated or otherwise distorted ventricular anatomy of a heart. In some embodiments, ventricular remodeling coil devices in accordance with the present disclosure at least partially prevent the continued enlargement of a ventricle (e.g., the left ventricle) of the heart and/or preserve the function of one or more heart valves (e.g. the mitral valve), such as may be experienced after a heart trauma (e.g., myocardial infarct). For reference, the anatomy of the human heart is described in detail below with reference to FIG. 1.

Figure 1:
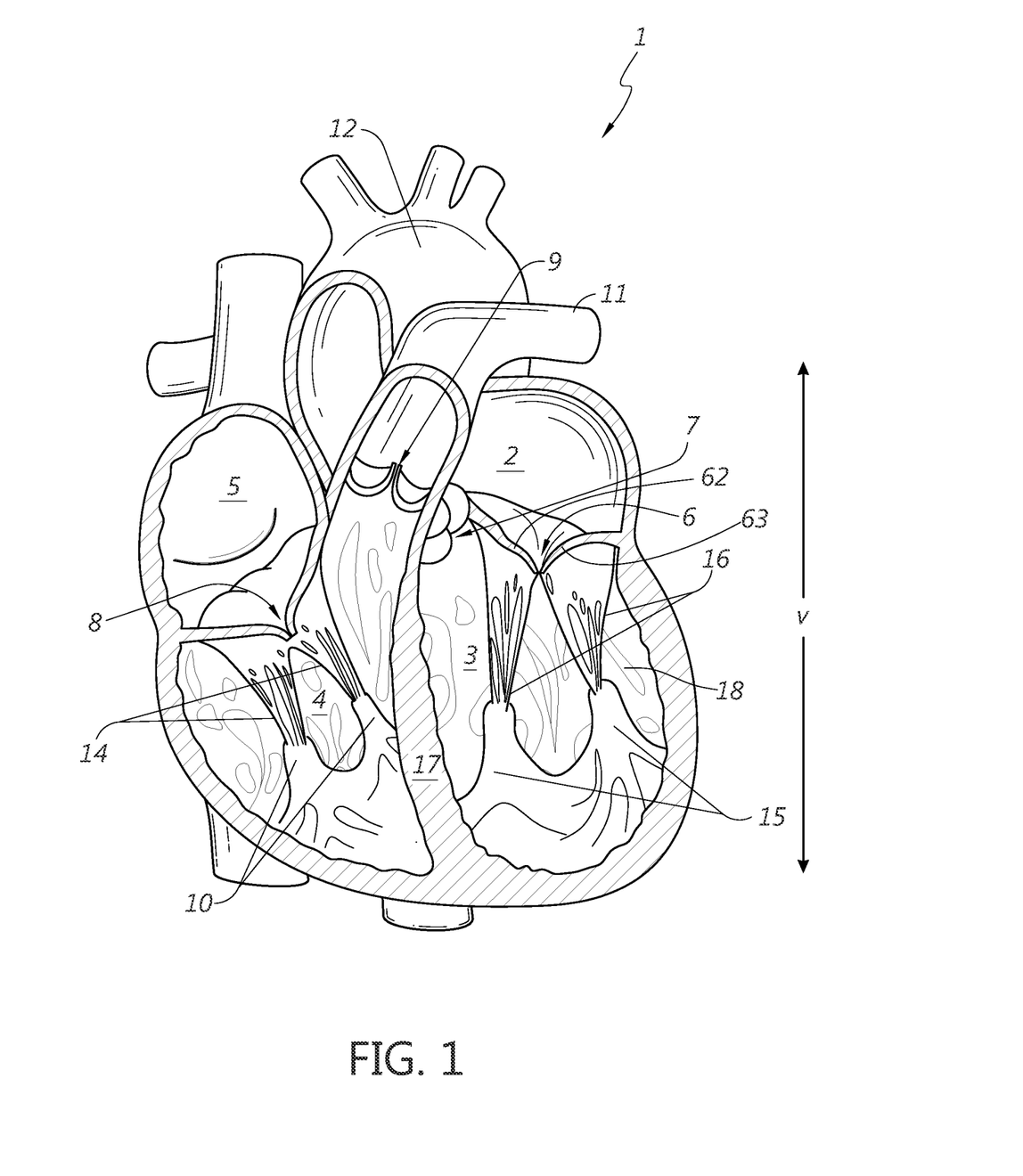
FIG. 1 provides a cross-sectional view of a human heart.

In humans and other vertebrate animals, the heart generally comprises a muscular organ having four pumping chambers, wherein the flow thereof is at least partially controlled by various heart valves. The two upper chambers of the heart are generally referred to as atria 2, 5, while the two lower chambers are generally referred to as ventricles 3, 4. A muscular septum 17 divides the heart 1 and separates the left ventricle 3 from the right ventricle 4. The septum 17 continues to divide the heart 1 and separates the left atrium 2 from the right atrium 5.

The heart valves, namely, the aortic, mitral (or bicuspid), tricuspid, and pulmonary valves, may be configured to open and close in response to a pressure gradient present during various stages of the cardiac cycle (e.g., relaxation and contraction) to at least partially control the flow of blood to a respective region of the heart and/or to blood vessels (e.g., pulmonary artery, aorta, etc.). The valves function to maintain the pressure and unidirectional flow of blood through the body and to prevent blood from leaking back into a chamber from which it has been pumped.

The two valves that separate the atria 2, 5 from the ventricles 3, 4, can be referred to as atrioventricular valves. The left atrioventricular valve, the mitral valve 6, controls the passage of oxygenated blood from the left atrium 2 to the left ventricle 3. A second valve associated with the left ventricle 3, the aortic valve 7, separates the left ventricle 3 from the aortic artery (aorta) 12, which delivers oxygenated blood to the entire body. The aortic valve 7 and mitral valve 6 can be considered part of the "left" heart, which controls the flow of oxygen-rich blood from the lungs to the body. The right atrioventricular valve, the tricuspid valve 8, controls passage of deoxygenated blood from the right atrium 5 into the right ventricle 4. The pulmonary valve 9 separates the right ventricle 4 from the pulmonary artery 11. The right ventricle 4 pumps deoxygenated blood through the pulmonary artery 11 to the lungs, wherein the blood is oxygenated by the lungs and then delivered to the left atrium 2 via the pulmonary vein. Accordingly, the tricuspid valve 8 and pulmonary valve 9 can be considered part of the "right" heart, which controls the flow of oxygen-depleted blood from the body to the lungs.

Both the left and right ventricles 3, 4 constitute "pumping" chambers. The aortic valve 7 and pulmonary valve 9 lie between a pumping chamber (ventricle) and a major artery and control the flow of blood out of the ventricles and into circulation. The aortic valve 7 and the pulmonary valve 9 generally have three cusps, or leaflets, that open and close in a one-way fashion, and thereby function to prevent blood from leaking back into the ventricles after being ejected therefrom for circulation.

Both the left and right atria 2, 5 can be considered "receiving" chambers. The mitral valve 6 and tricuspid valve 8, therefore, lie between a receiving chamber (atrium) and a ventricle so as to control the flow of blood from the atria to the ventricles and prevent blood from leaking back into the atrium during ejection into the ventricle. The mitral valve 6, generally includes two cusps, or leaflets, and the tricuspid valve 8 generally includes three cusps, or leaflets. The mitral valve 6 and the tricuspid valve 8 are encircled by a variably dense fibrous ring of tissues known as the annulus. The atrioventricular valves 6, 8 are anchored to the walls of the ventricles by respective chordae tendineae (chordae) 16, 14. The chordae tendineae 16, 14 comprise cord-like tendons that connect papillary muscles 15, 10 of the respective ventricle to the respective valve leaflets of the mitral valve 6 and tricuspid valve 8.

Certain description of the heart anatomy below, as well as certain embodiments or features of the present inventive solutions, are described in the context of the left ventricle. However, it should be understood that the anatomy and/or concepts disclosed are applicable to the right atrium and corresponding anatomical features thereof. With respect to the left ventricle 3, the ventricle 3 includes papillary muscles 15, which are generally coupled at their base to the ventricle wall(s) and are tethered to the leaflets of the mitral valve 6 via the chordae 16. The papillary muscles 15 may generally serve to limit the movement of the leaflets of the mitral valve 6 and prevent the valve leaflets from becoming inverted (e.g., prolapsed), whereas the papillary muscles 10 (and chordae 14) generally serve to limit the movement of the leaflets of the tricuspid valve 8. The papillary muscles do not open or close the valves of the heart, which close passively in response to pressure gradients; rather, the papillary muscles brace the valve leaflets against the high pressure needed to circulate the blood throughout the body. Together, the papillary muscles 15, 10 and the respective chordae tendineae 16, 14 can be referred to as the sub-valvular apparatus. The function of the sub-valvular apparatus is to keep the associated valve leaflets from prolapsing into the atria when they close.

The mitral valve 6 includes two leaflets, the anterior leaflet 62 and the posterior leaflet 63, and a diaphanous incomplete ring around the valve, called the annulus. The mitral valve 6 is generally associated with two papillary muscles 15, the anteromedial and the posterolateral papillary muscles, which attach the leaflets 62, 63 to the walls of the left ventricle 3 via the chordae tendineae 16. The tricuspid valve 8 typically is made up of three leaflets, coupled to three papillary muscles. However, the number of leaflets can range between two and four. The three leaflets of the tricuspid valve 8 are referred to as the anterior, posterior, and septal leaflets. Although both the aortic 7 and pulmonary 9 valves each have three leaflets (or cusps), they do not have chordae tendineae.

The ventricles of the heart 1 further include trabeculae carneae ("trabeculae" herein) associated with the inner ventricle walls. The trabeculae 18 can comprise irregular bands and bundles of muscle associated with and/or projecting from the inner surfaces of the ventricles. The trabeculae 18 may be concentrated at or near the apex of the ventricles, but may also span all or part of a circumferential dimension and/or vertical dimension (dimension in FIG. 1) of the inner walls (i.e., sidewalls) of the ventricles. The trabeculae 18 may form prominent ridges, or gaps, which may be leveraged for inserting or weaving coil device features therein or therethrough, as described in detail below in connection with one or more embodiments of the present disclosure.

Over time, or as a result of a heart attack (i.e., myocardial infarction secondary to coronary artery disease) or other heart diseases (e.g., cardiomyopathy), the geometry of the ventricle(s) (e.g., left ventricle) and/or valve(s) (e.g., mitral valve) of the heart can become at least partially distorted, causing cardiac dysfunction. For example, distortion of the heart geometry may take the form of ventricular dilation, wherein the size of the ventricular cavity, or cavities, is increased. Embodiments disclosed herein provide devices and methods for reducing or constricting ventricular dilation.

Figure 2:
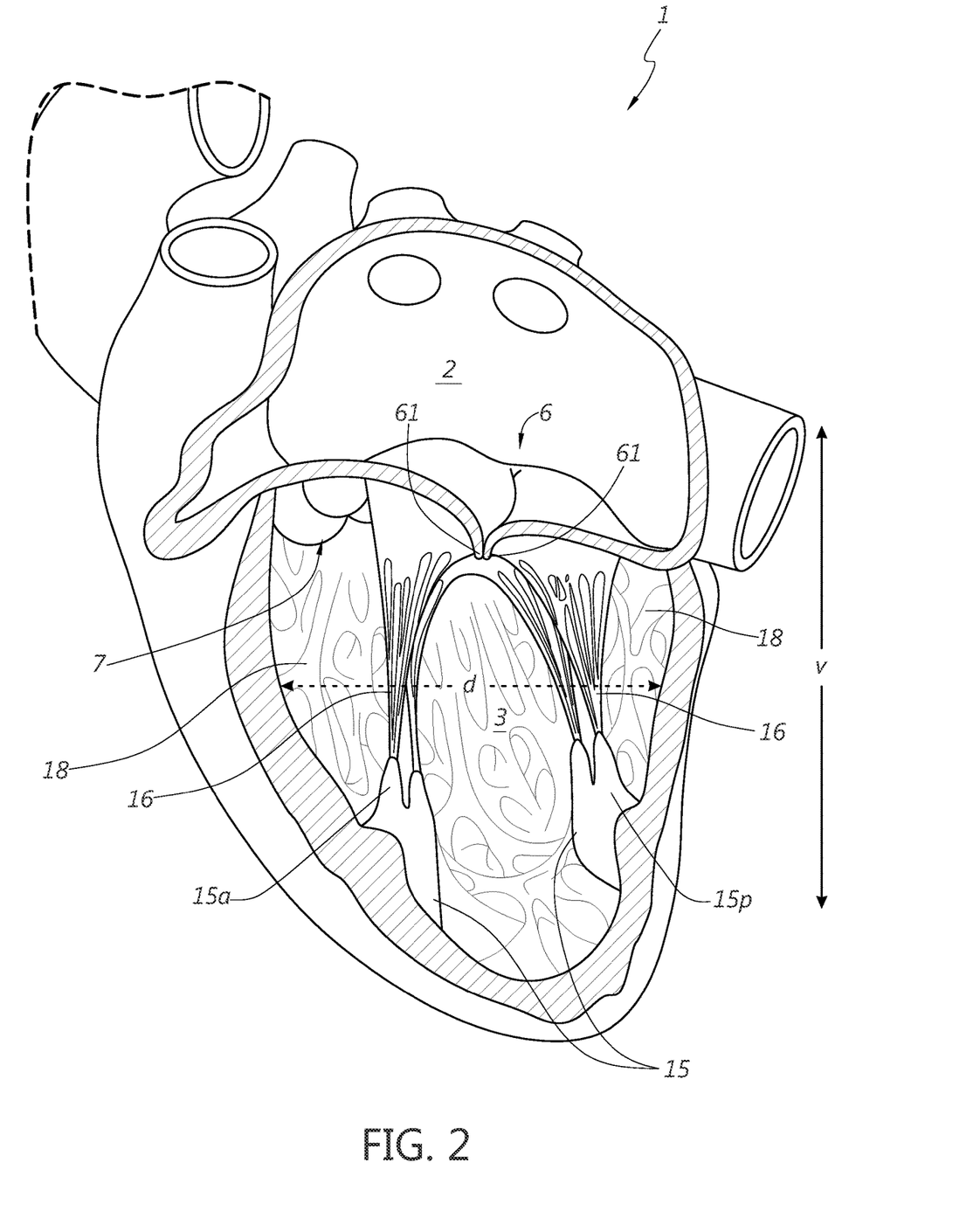
FIG. 2 provides a cross-sectional view of the left ventricle and left atrium of an example heart.

For reference, FIG. 2 provides a cross-sectional view of the left ventricle 3 and left atrium 2 of the example heart 1 shown in FIG. 1. The diagram of FIG. 2 shows the mitral valve 6, wherein the disposition of the valve 6, papillary muscles 15*a*, 15*p* and/or chordae tendineae 16 may be illustrative as providing for proper coapting/coaptation of the valve leaflets 61 to advantageously at least partially prevent regurgitation and/or undesirable flow into the left atrium 2 from the left ventricle 3, and vice versa. Although a mitral valve 6 is shown in FIG. 2 and various other figures provided herewith, and described herein in the context of certain embodiments of the present disclosure, it should be understood that ventricle remodeling principles disclosed herein may be applicable with respect to any atrioventricular valve, ventricle, and/or associated anatomy (e.g., papillary muscles, chordae tendineae, trabeculae carneae, ventricle wall, etc.), such as that associated with the right ventricle.

As described above, with respect to a healthy heart valve as shown in FIG. 2, the valve leaflets 61 may extend inward from the valve annulus and come together in the flow orifice to permit flow in the outflow direction (e.g., the downward direction with respect to the dimension in FIG. 2) and prevent backflow or regurgitation in the inflow direction (e.g., the upward direction with respect to the dimension in FIG. 2). For example, during atrial systole, blood flows from the atrium 2 to the ventricle 3, resulting in the chordae tendineae 16 being relaxed due to the atrioventricular valve 6 being forced open. When the ventricle 3 contracts during ventricular systole, the increased blood pressures in both chambers may push the valve 6 closed, preventing backflow of blood into the atria 2. Due to the lower blood pressure in the atria compared to the ventricles, the valve leaflets may tend to be drawn toward the atria. The chordae tendineae 16 can serve to tether the leaflets and hold them in a closed position when they become tense during ventricular systole. The papillary muscles 15 provide structures in the ventricles for securing the chordae tendineae and therefore allowing the chordae tendineae to hold the leaflets in a closed position. The papillary muscles 15 may include an anterolateral papillary muscle 15*a*, which may be tethered primarily to the anterior leaflet, for example, and a posteromedial papillary muscle 15*p*, which may be tethered primarily to the posterior leaflet, for example. With respect to the state of the heart 1 shown in FIG. 2, the proper coaptation of the valve leaflets, which may be due in part to proper geometry of the ventricle 3 and/or position of the papillary muscles 15, may advantageously result in mitral valve operation substantially free of leakage. The example healthy heart shown in FIG. 2 has a ventricular diameter d at or near a vertical mid-point (with respect to the illustrated vertical dimension V).

As referenced above, ventricular dilation is a condition wherein the wall of the heart muscle thins and/or expands as compared to a healthy heart (see FIGS. 1, 2). For a variety of reasons, a dilated ventricle may exhibit, or be associated with, a reduced ability of the heart/ventricle to pump blood. As a result, ventricular dilation may increase the load on the heart while decreasing cardiac efficiency. One reason for an increased load on the heart due to the presence/occurrence of ventricular dilation is that blood may be pumped in a direction other than directly towards the heart valve (e.g., aortic valve 7). Another reason for the increased load on the heart can be that the enlarged ventricle can negatively affect the operation of one or more heart valves. More particularly, if the leaflets of a heart valve are not aligned properly due to an enlarged valve annulus caused by ventricular dilation, the leaflets may not close sufficiently tightly. Incomplete leaflet closure, as described above, can result in regurgitation of blood through the valve. Ventricular dilation is a relatively common condition in elderly people that contributes to fatigue when performing physical activities, such as walking. Unfortunately, in many cases, patients suffering from ventricular dilation may lead relatively limited lives due to the impaired function of the heart.

As described briefly above, valve regurgitation (e.g., functional mitral regurgitation (FMR)) may be caused at least in part by ventricular dilation, which may cause geometrical distortion of the heart anatomy resulting in the leaflets of a heart valve (e.g., mitral valve) not closing completely, thereby causing blood to leak back into the prior chamber. Ventricular dilation can cause dilation of the heart valve annulus, resulting in a Carpentier's type I malfunction wherein normally functioning leaflets are distracted from each other and fail to form a tight seal (i.e., do not coapt properly). Furthermore, ventricular dilation can result in prolapse of one or more leaflets above the plane of coaptation thereof, which may be referred to as a Carpentier's type II malfunction. In some cases, the dilation of the ventricle can cause the stretching or rupturing of chordae tendineae normally connected to the leaflet(s). Ventricular dilation can further cause a restriction of the motion of one or more leaflets such that the leaflets are abnormally constrained below the level of the plane of the annulus. Such condition may be referred to as a Carpentier's type III malfunction.

Figure 3:
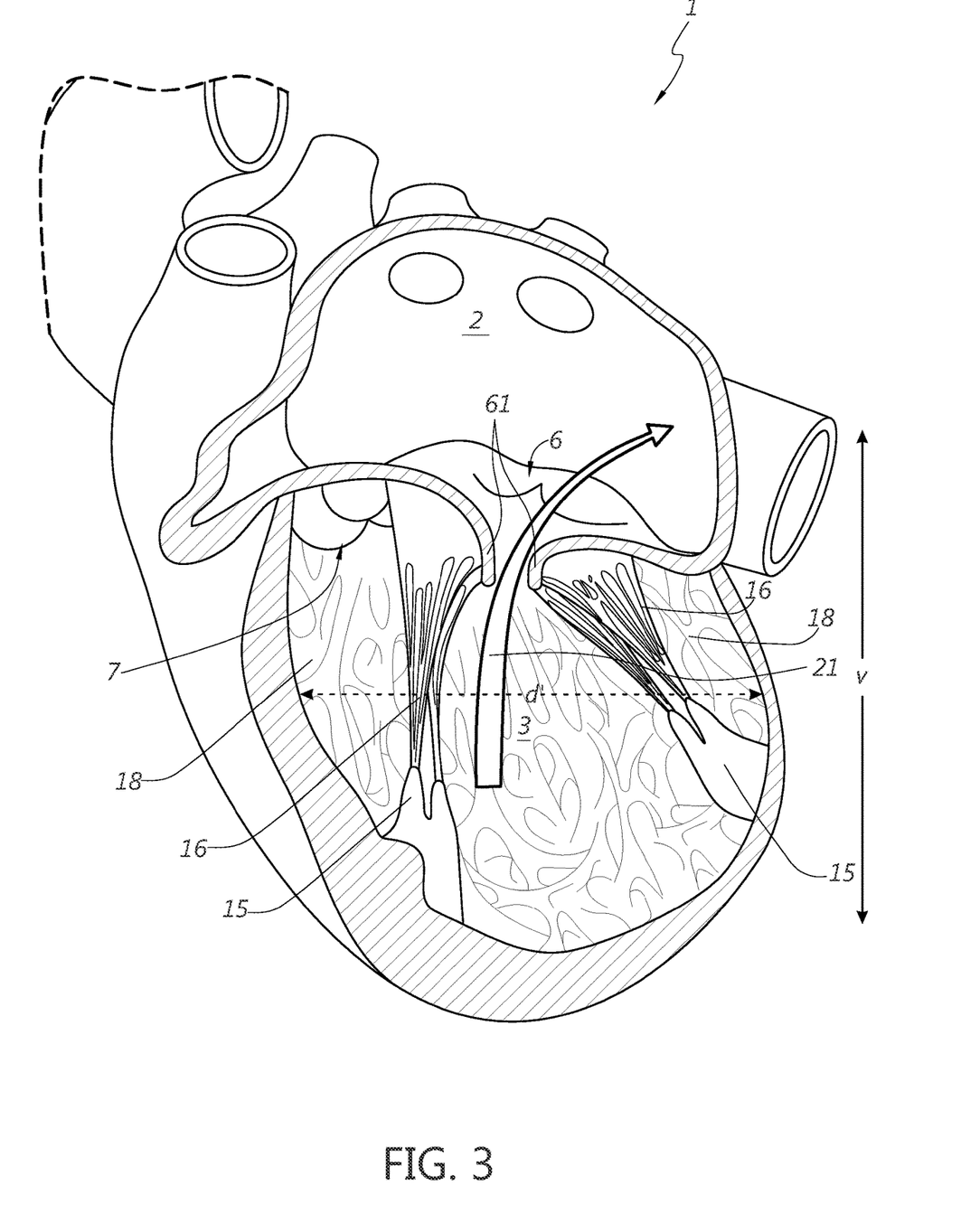
FIG. 3 provides a cross-sectional view of an example heart experiencing ventricular dilation.

Due to ventricular dilation or geometric distortion, the position of papillary muscles may become altered, thereby potentially contributing to valve regurgitation. For example, as shown in FIG. 3, which illustrates a cross-sectional view of a heart 1 experiencing ventricular dilation and resulting mitral regurgitation flow 21; dilation of the left ventricle may cause changes in the position of the papillary muscles 15, and/or other anatomical distortion, that allow the flow 21 back from the ventricle 3 to the atrium 2. The example dilated heart shown in FIG. 3 has a ventricular diameter d' at or near a vertical mid-point (with respect to the illustrated vertical dimension 'v'), which represents a greater diameter than the diameter d of the healthy heart shown in FIG. 2 at the same vertical offset. As referenced above, dilation of the left ventricle can be caused by any number of conditions, such as focal myocardial infarction, global ischemia of the myocardial tissue, or idiopathic dilated cardiomyopathy, resulting in alterations in the geometric relationship between papillary muscles and other components associated with the valve(s) that can cause valve regurgitation. The resultant volume overload associated with ventricular dilation may increase chamber wall stress, resulting in valve dysfunction and degraded cardiac efficiency. If left untreated, the functional mitral valve regurgitation experienced in a heart like that shown in FIG. 3 may overload the heart 1 and can possibly lead to or accelerate heart failure. Solutions presented herein provide devices and methods for remodeling and/or constricting the ventricular wall(s) (e.g., of the left ventricle) and/or moving the papillary muscles 15 closer together (e.g., closer to their previous position), which may advantageously reduce the occurrence of mitral regurgitation.

In some implementations, embodiments of the present disclosure provide for treatment for patients suffering from ventricular dilation and/or papillary muscle displacement. Certain embodiments disclosed herein advantageously provide a sub-valvular solution for ventricular dilation and/or mitral regurgitation through papillary muscle approximation. The terms "approximation" and "papillary muscle approximation" are used herein according to their broad and/ordinary meanings and may refer to the manipulation or adjustment of a papillary muscle to bring the papillary muscle in closer proximity to another papillary muscle or anatomy of the heart.

Ventricular remodeling and/or papillary muscle approximation procedures may provide for at least partial reduction in left (and/or right) ventricular volume, reduction in recurrent mitral regurgitation, and/or other improvement in cardiac function. In some implementations, papillary muscle approximation can be performed surgically. However, such surgeries may be relatively difficult to teach and/or perform. Therefore, it may be desirable to implement ventricular remodeling/constriction and/or papillary muscle approximation through percutaneous approaches, which may provide access to therapy treating the underlying cause of functional mitral regurgitation to increased numbers of patients and/or physicians.

Certain embodiments disclosed herein provide solutions for ventricular dilation that involve ventricular constriction and/or papillary muscle re-positioning or adjustment. Solutions presented herein may be used to at least partially constrict the ventricular wall(s) and/or change the position of one or more papillary muscles in order to reduce the occurrences or severity of regurgitation, such as mitral regurgitation, and/or other cardiac inefficiency or dysfunction. As shown in FIG. 3, ventricular dilation can cause the papillary muscles 15 to move away from central axis (e.g., parallel to the illustrated vertical dimension V) of the valve or valve annulus, causing the chordae tendineae connecting the muscles to the leaflets to become undesirably tensioned/tethered. Such tensioning/tethering may restrict the leaflets from closing together properly, either symmetrically or asymmetrically, depending on the relative degree of displacement between the papillary muscles 15. Moreover, as the annulus dilates in response to ventricular enlargement and increased wall stress, increases in annular area and changes in annular shape may increase the degree of valve insufficiency.

Various techniques that suffer from certain drawbacks may be implemented for treating ventricular dilation and/or mitral valve dysfunction, including surgical repair or replacement of the diseased valve or medical management of the patient, which may be appropriate or effective primarily in early stages of mitral valve dysfunction during which levels of regurgitation may be relatively low. For example, such medical management may generally focus on volume reductions, such as diuresis or afterload reducers, such as vasodilators, for example. Valve replacement operations may also be used to treat regurgitation from valve dysfunction. However, such operations can result in ventricular dysfunction or failure following surgery. Further limitations to valve replacement solutions may include the potential need for lifelong therapy with powerful anticoagulants in order to mitigate the thromboembolic potential of prosthetic valve implants. Moreover, in the case of biologically-derived devices, such as those used as mitral valve replacements, long-term durability may be limited. Another commonly employed repair technique involves the use of annuloplasty rings to improve mitral valve function. An annuloplasty ring may be placed in the valve annulus and the tissue of the annulus sewn or otherwise secured to the ring. Annuloplasty rings can provide a reduction in the annular circumference and/or an increase in the leaflet coaptation area. However, annuloplasty rings may flatten the saddle-like shape of the valve and/or hinder the natural contraction of the valve annulus. Successful treatment or correction of ventricular dilation can result in improved valve function (e.g., reduction in regurgitation) and/or improved cardiac efficiency. Treatments for ventricular dilation may involve utilizing external supports, such as sacs or wraps, which are configured to be placed around the exterior of the heart to restrict the ventricular walls in an effort to improve its pumping efficiency. Other treatments can involve surgically remodeling the ventricle by removing a portion of the muscular wall. In addition, certain pharmacological treatments may be used, such as diuretics, and/or mechanical pump devices may be used to reduce the load on the heart by assisting with the pumping function normally performed by the heart. With respect to surgical techniques for treating ventricular dilation and/or valve dysfunction, such techniques may suffer from various limitations, such as requiring opening the heart to gain direct access to the valve and the valve annulus. Therefore, cardiopulmonary bypass may be required, which may introduce additional morbidity and mortality to the surgical procedures. Additionally, for surgical procedures, it can be difficult or impossible to evaluate the efficacy of the repair prior to the conclusion of the operation.

The various treatments referenced above suffer from various drawbacks and may not be appropriate for patients that are already in a weakened cardiac condition. Therefore, due to the invasive nature and other drawbacks associated with certain ventricular dilation treatments, some patients suffering from ventricular dilation may not receive adequate treatment.

Disclosed herein are devices and methods for treating ventricular dilation and valve dysfunction without the need for cardiopulmonary bypass and without requiring major remodeling of the ventricle or dysfunctional valve. In particular, passive techniques to change the shape and/or position of the ventricle wall and/or the papillary muscles are disclosed. Furthermore, various embodiments disclosed herein provide for the treatment of ventricular dilation and valve dysfunction that can be executed on a beating heart, thereby allowing for the ability to assess the efficacy of the ventricular remodeling treatment and potentially implement modification thereto without the need for bypass support. In some implementations, the present disclosure provides devices and methods for reducing left ventricular volume and/or relieving leaflet tethering via papillary muscle approximation. Such devices/methods may advantageously utilize coil-type devices or mechanisms. Although certain surgical procedures may be implemented for ventricular remodeling and/or papillary muscle approximation, as described above, certain embodiments of the present disclosure advantageously provide for percutaneous access to the ventricle, papillary muscles, and/or associated anatomy, which may be safer and/or easier to execute relative to certain surgical procedures, and therefore may allow for a relatively greater number or percentage of potential patients to be eligible for valve treatment through papillary muscle approximation.

According to some ventricular remodeling solutions, the left ventricle wall is engaged by one or more tissue anchors into and/or through the left ventricular wall. However, such solutions can result in relatively negative patient responses. Certain embodiments disclosed herein advantageously utilize a coil device configured to engage the trabeculae carneae ("trabeculae") and/or other ventricular anatomy and constrict the ventricular wall(s) without the need for tissue-damaging tissue anchors and/or through-wall puncturing.

According to some mitral valve correction solutions, a coil is used to wind around or near the annulus of the mitral valve to provide a docking structure for a prosthetic heart valve (e.g., transcatheter heart valve). However, such coil solutions may not adequately provide for continued left ventricle engagement/constriction. Certain embodiments disclosed herein advantageously leverage a coil device delivered to the ventricle (e.g., left ventricle) percutaneously (e.g., using a transseptal puncture), wherein the coil device is used to gather the ventricular anatomy (e.g., trabeculae and/or papillary muscles) and pull the ventricular wall and/or papillary heads closer together. Constriction of the left ventricle using a permanent coil device implant in accordance with embodiments of the present disclosure may advantageously reduce the left ventricular volume indefinitely or permanently and/or correct or improve any mitral regurgitation that may have existed. In some embodiments, the coil device may be cinched using a draw-string-type feature and/or a pre-shaped coil, which may allow for the coil device to pull the ventricular anatomy together.

Ventricular Remodeling/Constriction Using Coil Device

As shown in FIG. 3 and described above, papillary muscle displacement and other structural defects caused by ventricular dilation may cause or affect leaflet tethering, loss of coaptation, regurgitation, and/or other complications. The present disclosure provides devices and methods for remodeling the ventricle(s) of the heart using trabeculae carneae ("trabeculae") and/or papillary muscle capturing. Although certain embodiments are disclosed herein in the context of left ventricle constriction and/or papillary muscle adjustment or manipulation, it should be understood that the principles disclosed herein are applicable to the right ventricle, and associated anatomy and conditions.

When the ventricle dilates, the stretching-out of the heart muscle can affect the ability of the heart to pump blood. Embodiments of the present disclosure serve to bring the ventricle back to a position where the heart can properly flex, thereby helping the heart to regain the ability to pump blood. In some implementations, the present disclosure provides a coil-type device delivered to the ventricle, such as through a transcatheter procedure (e.g., using a transseptal puncture), wherein the coil device is used to gather the patient's anatomy (e.g., papillary muscle head(s) and/or trabeculae) and pull the ventricular walls and/or papillary heads closer together. Pulling the ventricular walls and/or papillary muscle heads together can be achieved by, for example, cinching the coil device with a draw string feature, or through the use of a pre-shaped coil (e.g., memory metal) to pull the ventricular anatomy together.

Figure 4:
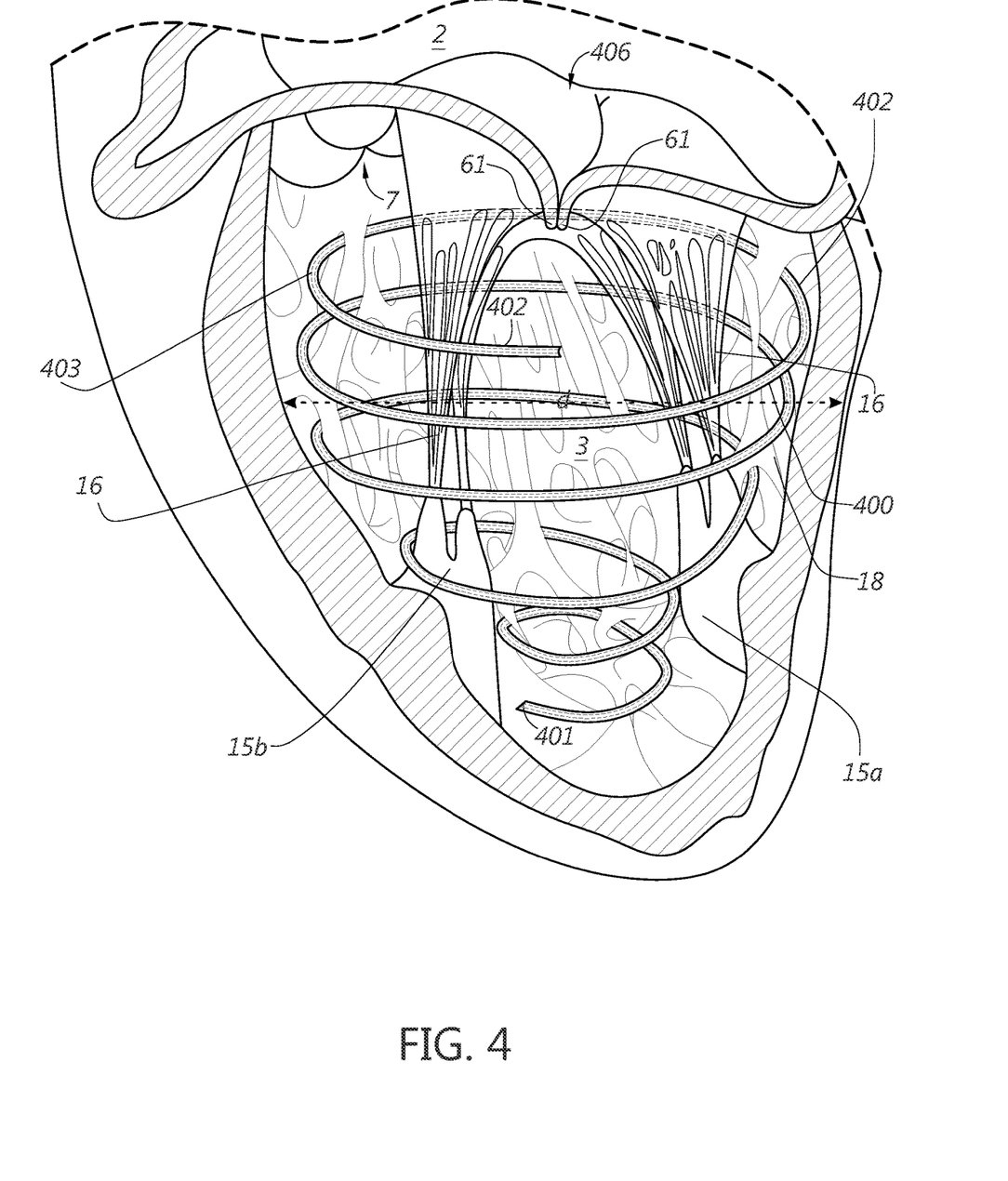
FIG. 4 illustrates a coil device deployed in a ventricle of a heart in accordance with one or more embodiments.

FIG. 4 illustrates a ventricle remodeling/constriction coil device 400 in accordance with one or more embodiments. In some implementations, coil device 400 has a helical form or shape when implanted in a ventricle of a heart. The coil device 400 may comprise memory metal (e.g., Nitinol), which may be configured to be delivered to the ventricle 3 using a delivery catheter and assume a cinched form after implantation in the ventricle 3 as shown in FIG. 4. For example, after deployment in the target ventricle, and around the captured anatomy, an electrical charge may be employed to cause the coil device to assume a tightened shape. Alternatively, the thermal environment of the target ventricle may induce a tightening in the coil device to assume a pre-shaped form. In some embodiments, the coil device may be transported to the target ventricle in a cooled state, such that the shaping/tightening of the coil does not substantially occur until after deployment and/or implantation of the coil device. Although electrical and thermal stimuluses are described herein, it should be understood that the coil device may be configured to assume a pre-shaped form or shape in response to any type of stimulus.

The coil device 400 may be configured to be delivered to the ventricle of a heart using a transcatheter approach. In certain embodiments, the coil device 400 comprises a helical form that is configured and/or designed to wrap along or near the inner ventricular wall, and/or around one or more papillary muscles 15 in the ventricle. The coil device 400 may be configured to be transported within a delivery system (e.g., delivery catheter) in a compressed configuration, wherein the coil device may assume an expanded configuration as it is deployed from the delivery system.

The coil device 400 may comprise a wire or suture component 403. The term "suture" is used according to its plain and ordinary meaning and may refer to any elongate strip, strand, line, tie, string, ribbon, strap, or other type or form of material used in medical procedures. One having ordinary skill in the art will understand that a wire, tube, pipe, or other similar structure or material may be used in place of a suture. Although certain embodiments are described herein in the context of wire-based coil devices, it should be understood that such description is applicable to suture-type cinching devices or devices having any suitable material or form. The wire 403 may comprise any suitable material, including metal, polymer, or the like. In some embodiments, the wire/suture 403 provides a passive spring-type element for pulling the ventricular anatomy with which it is engaged inward. The wire 403 provides inward cinching force to thereby manipulate one or more anatomical features of the ventricle 3, such as the ventricle walls (through connection to the trabeculae), and/or the papillary muscle(s) 15a, 15b.

In some embodiments, the coil device 400 includes an outer cloth or other tissue-interface layer 402, which may serve as a passive tissue interface. In some implementations, the cloth 402 may have a sleeve form, tube form, or other form configured to form an interface with the contacting tissue. In some embodiments, the cloth 402 or wire 403 components may be associated with one or more tissue anchor features, such as one or more microanchors, barbs, or the like, wherein such features may be configured to engage the wall of the ventricle or other anatomy associated therewith in order to provide increased engagement with the ventricular tissue. In some embodiments, the cloth 402 provides full circumferential covering of the wire 403. The cloth may promote in-growth with the contacting ventricular tissue, wherein the coil device 400 may become at least partially encapsulated with in-growth over time. For example, the cloth may comprise pores of a size sufficient to allow blood to at least partially seat therein, thereby allowing for the endothelium layer of the surrounding tissue to in-grow into the cloth. In such embodiments, the friction between the coil device 400 and the contacting tissue during pumping of the heart may be reduce or eliminated. Although certain embodiments are described as having a cloth feature that promotes ingrowth, it should be understood that such feature(s) may comprise or consist of non-cloth material designed to promoted tissue ingrowth. In some embodiments, the coil device 400 does not comprise a tissue-interface cloth.

The coil device 400 can advantageously be weaved or threaded behind ridges or features of the trabecula at one or more points along the circumference and/or height (with respect to the illustrated vertical dimension 'v' and the orientation shown in FIG. 4) of the ventricular wall to form one or more vertically-offset coils, as shown. For example, the trabeculae may generally have cobweb-like tissue features, wherein the coil device 400 can become intentionally entangled behind or within such tissue features, as shown. For example, the tissue features of the trabeculae may present gaps between ridges or other features, wherein the distal end of the coil device 400 can be navigated into such gaps and/or behind ridges in the trabeculae tissue. Although capturing of trabeculae and papillary muscles by coil devices is described herein, it should be understood that the coil device 400 may leverage any structural element inside the ventricle of the heart. As shown in FIG. 4, the coil device 400 may be wrapped at least partially around the inner wall of the ventricle and may further be cinched or tightened to some degree to draw the captured tissue/structure inward. In some embodiments, the coil device 400 is tightened using a drawstring feature or mechanism (not shown). For example, the drawstring feature or mechanism may comprise cord lock, or cord fastener, component. The cord lock/fastener component may be configured to attaches to one or more portions of the coil device, such as to the distal end thereof, and may be able to secure the coil device in a tightened state without the use of knots.

The cord lock/fastener feature of the drawstring mechanism may comprise a barrel, a toggle (i.e., plunger), and/or a spring component. In certain embodiments, squeezing the toggle component may allow for tension in the cord lock/fastener to be released, such that the coil device can be moved or adjusted therein. Releasing the toggle may cause the tension in the spring or other tensioning element to be engaged to thereby secure the coil device relative to the cord lock/fastener. The cord lock/fastener may be a relatively miniaturized cord lock/fastener, and may be a spring-type, non-spring-type, or rim-type cord lock/fastener. The drawstring mechanism and/or cord lock/fastener may be used to retain one or more segments or portions of the coil device (e.g., a wire component thereof) in a tightened condition, and may allow for the release of such soil segment(s) when desired. The cord lock/fastener may be fixedly coupled to a first portion of the coil device (e.g., the distal or proximal end portion of coil device), and may allow for a second portion of the coil device (e.g., the distal or proximal end portion of the coil device) to be inserted therein and secured within the cord lock/fastener to thereby lock the second portion in a fixed position relative to the cord lock/fastener and/or the first portion of the coil device.

In some embodiments, the wire 403 comprises a coil or wire form, which may incorporate a spring-type mechanism configured to draw the device 400, and with it the ventricle wall(s), inward. The wire 403 may comprise shape memory metal, or other type of metal or at least partially rigid material. The inner wire 403 may advantageously be configured to assume a desired shape memory once deployed in the ventricle.

In some embodiments, the coil device 400 is integrated with a heart valve docking structure. For example, the coil device 400 may be integrated with a docking structure comprising a wire structure wrapped around a valve annulus to artificially create stenosis to provide a relatively rigid annulus for docking a replacement heart valve thereon. For example, the ventricular constriction coil may be a continuation of the coil wrapped around the annulus to provide a valve docking structure.

Although the coil device 400 is shown as being wrapped around the inner ventricle wall helically over substantially the whole height of the inner ventricle wall (with respect to the vertical dimension V), it should be understood that coil devices in accordance with the present disclosure may span or cover any circumferential or vertical area or region of the ventricle. For example, the coil device 400 may be disposed in only a lower portion of the ventricle in some embodiments and may cover only a vertical band area of the inner ventricle wall.

In addition to, or as an alternative to, the coil device 400 being woven behind or captured in trabeculae, in some embodiments, the coil device is configured to capture one or more papillary muscles or papillary muscle heads. For example, the coil device 400 is shown in FIG. 4 as being wrapped around the papillary muscle 15a and the papillary muscle 15b.

With the coil device 400 woven through the trabeculae and/or around other structural features of the ventricle 3, the coil device 400 may advantageously exert an inward force along some or all of the ventricle through the application of force to the captured tissue/structure. Where at least a portion of the coil device 400 abuts one or more of the papillary muscles on an outer side thereof, the coil device 400 may further directly approximate the papillary muscles. For example, when contacting an outer surface or portion of a papillary muscle, the coil device 400 may exert an inward force thereon to thereby move or approximate the papillary muscle(s). Such papillary muscle approximation may advantageously result in valve correction, wherein the leaflets 61 of a valve 406 associated with the ventricle 3 (e.g. mitral valve) may be brought into coaptation as to prevent or reduce the occurrence of regurgitation. The implantation of the coil device 400, in its tightened state, may reduce the diameter of the ventricle to a diameter d that is smaller than the diameter d' of the dilated ventricle shown in FIG. 3.

The coil device 400 and/or wire feature 403 thereof may advantageously have a sufficient thickness to prevent the coil device 400 from tearing through the captured ventricular tissue, or otherwise damaging the same, when the coil device rubs or is pulled against such tissue. For example, when implanted, certain friction/abrasion of the coil device 400 against the captured tissue may result from the beating of the heart 1. In some embodiments, the coil device 400 is configured to at least partially become in-grown with the trabeculae tissue and/or other tissue of the ventricle. In some embodiments, the coil device 400 comprises relatively lubricious material (e.g., Teflon™) to at least partially reduce friction/abrasion. For example, the coil device 400 may comprise material having a coefficient of friction less than or equal to about 0.1, as measured against polished steel. However, such embodiments may not in-grow with the contacting tissue, and therefore may be undesirable in some cases. In some embodiments, the movement of the coil device 400 against the contacting tissue over many cardiac cycles may cause scarring in the tissue, thereby protecting the tissue from further damage from abrasion.

In some embodiments, a distal end 401 of the coil device 400 is anchored or secured in some manner to the wall or tissue of the ventricle 3. For example, the distal end 401 may be anchored to the ventricular tissue at or near the apex of the heart/ventricle. Once anchored, tension may subsequently be applied to cinch or draw inward the coils of the coil device 400, to thereby reshape the ventricle. In some implementations, the coil device 400, or portion thereof, may be thermally or electrically activated/activatable, wherein an application or exposure to a certain temperature (or temperature range) or electrical charge may cause the coil device 400, or portion thereof, to expand or contract.

Ventricular Remodeling/Constriction Processes

Figure 5:
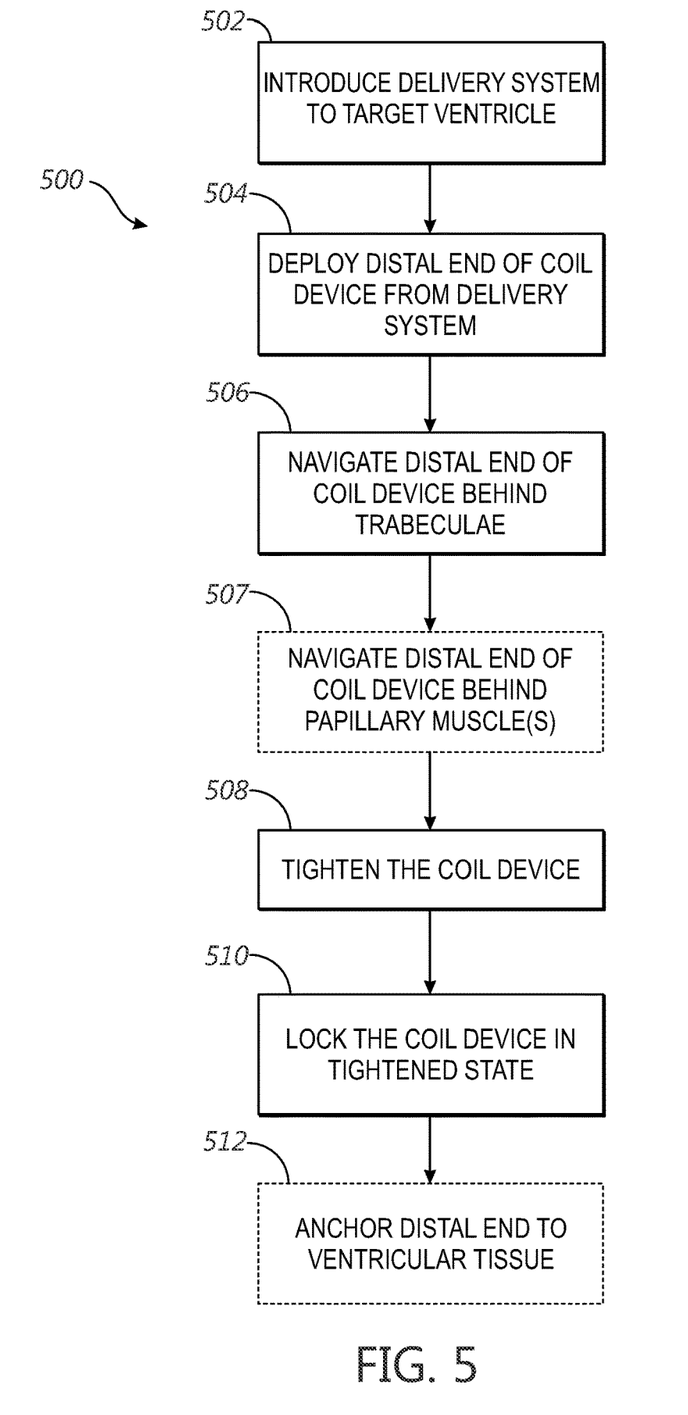
FIG. 5 is a flow diagram illustrating a process for remodeling a heart ventricle using a coil device in accordance with one or more embodiments.

FIG. 5 illustrates a process 500 for constricting a ventricle of a heart in accordance with one or more embodiments. At block 502, the process 500 involves introducing a coil device delivery system to a target ventricle of a heart. For example, the target ventricle may be dilated, wherein implantation of the coil device within the ventricle may be desirable to at least partially constrain the ventricle. For example, as referenced above, dilation of the inferior ventricular wall can cause the posteromedial papillary muscle(s) to distend laterally and/or apically. Distention of the papillary muscle(s) can result in a regurgitant jet or flow at or near the medial scallop (P3) of the posterior leaflet of the mitral valve. The process 500 may be implemented to at least partially correct or prevent dilation of the target ventricle and/or distention or displacement of the papillary muscles.

In some embodiments, the delivery system is advanced to the target ventricle percutaneously, such as through a transcatheter procedure. For example, the delivery system may be introduced to the target ventricle using a transseptal puncture from the right atrium into the left atrium, and down into the left ventricle through the mitral valve. The delivery system may be provided to the right atrium through the inferior vena cava (e.g., through a femoral artery access point) or superior vena cava (e.g., through jugular vein access point). In some embodiments, the delivery system is introduced into the left atrium (or right atrium) through a transapical procedure through a left (or right) ventricular apex puncture.

At block 504, the process 500 involves deploying a distal end of a coil device from the delivery system. At block 506, the process 500 involves navigating the distal end of the coil device behind and/or through one or more tissue features of trabeculae carneae within the ventricle. For example, the coil may be wrapped at least partially inside or behind the trabeculae and/or other anatomy (e.g., papillary muscle(s)) in the ventricle. Wrapping the coil device around the inner wall of the ventricle behind trabeculae features may form one or more helical coils around the inner wall of the ventricle, as shown in FIG. 4.

In some embodiments, the coil device comprises cloth or other material designed to promote ingrowth, such as cloth or the like. In some embodiments, the cloth is part of an outer sleeve or covering of the coil device. Where a cloth component is employed, the cloth may be able to move or slide relative to a more rigid wire component or may be fixed to the wire component at one or more points or regions.

The process 500 may further involve navigating the coil device around one or more papillary muscles or papillary heads, as shown at block 507. Where two papillary muscles are captured by the coil device, cinching or tightening of the coil device may result in approximation of the papillary muscles, which may provide certain benefits described in detail above. By navigating the coil device behind and/or through ridges or other features of trabeculae and/or around papillary muscles, the process 500 provides for the gathering-in of the patient's ventricular anatomy and pulling of the ventricular anatomy closer together to thereby at least partially reduce the volume of the ventricle and/or correct or reduce valve regurgitation (e.g., functional mitral regurgitation). In some embodiments, the process 500 involves capturing or grabbing as much of the ventricular anatomy as possible or desirable to increase the retention of the coil device and/or provide a relatively more robust connection to the ventricular wall itself. In some embodiments, only papillary muscle anatomy (e.g., papillary heads) is captured by the coil device. For example, where the trabeculae are too smooth or devoid of gaps to allow for capture thereof by the coil device, papillary muscles/heads may alternatively be captured.

The distal, or free, end 401 of the coil device may be wrapped around the inside of the ventricle wall, and behind one or more tissue features of the ventricle, as the coil device is pushed out of the delivery system (e.g., delivery catheter). This constriction/remodeling of the ventricle, once the coil has been navigated around the ventricular anatomy, can be achieved by the cinching or tightening of the coil device. At block 508, the process involves tightening or cinching the coil device (e.g., tightening or cinching one or more coils of the deployed coil device) to draw the captured anatomy inward, thereby constricting and/or remodeling the ventricle. For example, in some embodiments, the process 500 involves snaring the distal end of the coil device and drawing it back into the delivery system (e.g., delivery catheter), wherein as the end of the coil device is drawn or pulled, such action may cause the coil device to cinch down on itself to some degree, thereby tightening the coil(s) of the coil device, as desired. In some embodiments, cinching or tightening of the coil device is achieved using a drawstring tightening and/or locking feature. In some embodiments, tightening or cinching of the coil device is achieved through the use of a pre-shaped (e.g., memory metal) coil configured to assume a pre-shaped form after deployment and/or implantation thereof to pull the captured anatomy together. Embodiments incorporating pre-shaped memory metal coils may have one or more free ends of the coil after implantation that may be exposed within the ventricle. Cinching or tightening of the coil device may be implemented using a ratchet device or mechanism.

At block 510, the process 500 involves locking the coil device in a tightened or cinched position, state, or configuration. For example, the process may involve locking or securing the distal end of the coil device to a proximal end thereof, or to another portion of the coil device. Locking of the coil device may be implemented using any type of knot or locking mechanism. For example, the locking mechanism may comprise a piece of tubing or other material or form that is configured to allow a wire or suture to slide therethrough in one direction while preventing backing-out of the wire or suture in the opposite direction. The locking mechanism may secure a first portion of the coil device to a second portion of the coil device.

At block 512, the process 500 may involve anchoring the distal end of the coil device in ventricular tissue. For example, the distal end of the coil device may be anchored in ventricular tissue in an area at or near the apex of the ventricle/heart. In some embodiments, once anchored at the distal end, the coil device may slide or move within or against the trabeculae tissue, thereby providing force for moving the ventricle in or out without substantially resisting the actual active beating of the ventricle. In some embodiments, the coil device is fixed only at one end. As the heart beats, and the ventricle contracts, the coil device, or one or more components or portions thereof, may wind and unwind as the heart contracts and relaxes.

Although certain embodiments are described herein in the context of ventricular remodeling using coil devices, it should be understood that the principles disclosed herein apply to other types of device and processes for ventricular remodeling. For example, ventricular remodeling in accordance with aspects of the present disclosure may implement expandable, stent-like wall anchor(s) (e.g., which may have a form and/or function similar to rock climbing wedge and/or cam device), wherein a tether is coupled between such anchors to provide a tensioning force to pull tissue(s) associated with the anchors together. In some embodiments, ventricular remodeling is achieved using an epoxy form/material configured and disposed to cure in specific locations inside the heart, such as in connection with the trabeculae carneae, which may serve as anchor points to fixate a tether that provides tensioning force to pull the ventricle and/or papillary tissue together.

In some embodiments, the process 500 involves implanting or placing a valve leaflet spacer device. For example, the spacer device may be a plug or gap filler device configured to fill a gap or void between valve leaflets to reduce regurgitation. For example, the coil device may include one or more features to which the spacer device may be secured, or with which the spacer device may be at least partially integrated. In some embodiments, a wire or other line feature of the coil device may run across at least a portion of a diameter of the ventricle, wherein the spacer device is attached to or integrated with the wire/line. Such a configuration may advantageously promote ventricular contraction as the pressure in the heart chambers pulls the spacer device in a direction to at least partially tighten the coil device.

Additional Embodiments

Depending on the embodiment, certain acts, events, or functions of any of the processes described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

It should be understood that the claims and/or claim elements associated with the present application are not intended to invoke 35 U.S.C. 112(f) unless the words "means for" or "step for" are explicitly used in the particular claim.

What is claimed is:

1. A method for treating a heart valve, the method comprising:
    introducing a delivery catheter into a target ventricle of a heart, the delivery catheter having a coil device disposed at least partially therein;
    deploying a distal end of the coil device from the delivery catheter;
    navigating the distal end of the coil device behind a plurality of trabeculae carneae features on an inner wall portion of the ventricle that is above first and second papillary muscles of the ventricle with respect to a ventricle dimension to form a plurality of vertically-offset coils winding along the inner wall portion of the ventricle; and
    tightening the plurality of coils to reduce a diameter of the target ventricle by pulling the inner wall portion that is above the first and second papillary muscles inward.

2. The method of claim 1, wherein the coil device comprises:
    a cloth sleeve configured to promote ingrowth with tissue of the plurality of trabeculae carneae; and
    a wire disposed within the cloth sleeve;

wherein, the wire is permitted to slide longitudinally within the cloth sleeve as the heart cycles.

3. The method of claim 1, wherein said introducing the delivery catheter into the target ventricle is performed at least partially percutaneously.

4. The method of claim 3, further comprising introducing the delivery catheter into an atrium of the heart through a transseptal puncture.

5. The method of claim 1, further comprising navigating the distal end of the coil device along a helical path around the inner wall portion of the ventricle to form the plurality of coils.

6. The method of claim 1, further comprising navigating the distal end of the coil device around the first and second papillary muscles, wherein said tightening the plurality of coils approximates the first and second papillary muscles together.

7. The method of claim 1, wherein said tightening the plurality of coils comprises pulling the distal end of the coil device.

8. The method of claim 7, wherein said tightening the plurality of coils further comprises pulling the distal end of the coil device back into the delivery catheter.

9. The method of claim 1, further comprising, after said tightening the plurality of coils, locking the coil device in a tightened state.

10. The method of claim 9, wherein said locking the coil device in the tightened state is performed using a drawstring mechanism.

11. The method of claim 1, wherein the coil device comprises material that promotes ingrowth with tissue of the inner wall portion of the ventricle.

12. The method of claim 1, further comprising embedding the distal end of the coil device in tissue of the ventricle at an apex of the ventricle, such that the distal end of the coil device is embedded in the tissue of the ventricle and a proximal end of the coil device is free within the ventricle.

13. The method of claim 1, further comprising embedding the distal end of the coil device in tissue of the ventricle at an apex of the ventricle.

14. The method of claim 1, wherein the coil device comprises material having a coefficient of friction of less than or equal to 0.1.

15. The method of claim 1, wherein a thermal environment within the ventricle causes said tightening of the plurality of coils to assume a pre-shaped form of the coil device.

16. The method of claim 1, wherein the coil device is formed of a suture.

17. The method of claim 1, wherein the coil device comprises a cloth sleeve including one or more tissue anchors configured to engage the inner wall portion of the ventricle.

18. The method of claim 1, wherein said tightening of the plurality of coils is caused by spring tension in the coil device.

19. The method of claim 1, wherein the coil device comprises a cloth sleeve configured to promote ingrowth with tissue of the plurality of trabeculae carneae features and a wire disposed within the cloth sleeve.

20. The method of claim 1, wherein the coil device is formed of shape memory metal pre-shaped to form the plurality of vertically-offset coils.

* * * * *